United States Patent [19]

Usmani

[11] Patent Number: 5,081,278

[45] Date of Patent: Jan. 14, 1992

[54] PROCESS OF MAKING OPTIONALLY SUBSTITUTED ALKYL P-DIMETHYLAMINOBENZOATES

[75] Inventor: Atique A. Usmani, Castleford, England

[73] Assignee: Lambson Limited, London, England

[21] Appl. No.: 552,572

[22] Filed: Jul. 16, 1990

[30] Foreign Application Priority Data

Jul. 19, 1989 [GB] United Kingdom ............... 8916516

[51] Int. Cl.$^5$ .................. C07C 227/00; C07C 201/00
[52] U.S. Cl. ...................................................... 560/19
[58] Field of Search ........................................... 560/19

[56] References Cited

U.S. PATENT DOCUMENTS

| | | | |
|---|---|---|---|
| 4,002,664 | 1/1977 | Quadbeck-Seeger et al. | 260/471 R |
| 4,983,754 | 1/1991 | Eisenstadt | 560/19 |

FOREIGN PATENT DOCUMENTS

| | | | |
|---|---|---|---|
| 0245194 | 4/1987 | Fed. Rep. of Germany | 560/19 |
| 3269128 | 11/1988 | Japan | 560/19 |
| 0753069 | 7/1989 | U.S.S.R. | 560/19 |
| 1052610 | 12/1966 | United Kingdom | 560/19 |

*Primary Examiner*—Jose G. Dees
*Assistant Examiner*—Porfirio Nazario
*Attorney, Agent, or Firm*—Larson and Taylor

[57] ABSTRACT

An improved process for the production of alkyl or substituted alkyl p-dimethylamino benzoates by the reductive alkylation of alkyl or substituted alkyl p-aminobenzoates using hydrogen in the presence of raney nickel.

13 Claims, No Drawings

PROCESS OF MAKING OPTIONALLY SUBSTITUTED ALKYL P-DIMETHYLAMINOBENZOATES

BACKGROUND OF THE INVENTION

This invention relates to a process for production of alkyl or substituted alkyl p-dimethylaminobenzoates and in particular, though not exclusively to the production of ethyl p-dimethylaminobenzoate.

Alkyl p-dimethylaminobenzoates have previously been made by the reductive alkylation of alkyl p-aminobenzoates using formaldehyde in the presence of hydrogen and a catalyst, for example palladium on charcoal, under forcing conditions of temperature and pressure.

The reaction is a complex multi-stage mechanism, proceeding through reduction of intermediate Schiff's bases (formaldehyde-amine condensation products) and is difficult to take to completion even under the forcing conditions of temperature and pressure used. As a result, impurities from unreacted Schiff's bases and side reactions can typically be present in the product at up to 2% in total.

The alkyl p-dimethylaminobenzoates thus produced are used as photoinitiators in wide range of applications and the presence of such impurities may, in certain of these applications, adversely affect the photoinitiation properties. Also, the impurities may themselves be toxic or react during the photoinitiation process to produce side products that are toxic.

Removal of the impurities present in the alkyl p-dimethylaminobenzoates produced by the known process would add significantly to production costs.

It is an object of the present invention to provide a process for the production of alkyl or substituted alkyl p-dimethylaminobenzoates which mitigates the above-discussed problems of the known process.

SUMMARY OF THE INVENTION

According to the present invention I provide a process for the production of alkyl or substituted alkyl p-dimethylaminobenzoates by the reductive alkylation of alkyl or substituted alkyl p-aminobenzoates using formaldehyde in the presence of hydrogen and a catalyst characterised in that the catalyst is raney nickel.

We have found that using raney nickel as the catalyst results in unexpected and significant improvements as compared with the catalysts used in the prior art process. In particular, we have found that the reaction proceeds substantially to completion under milder conditions of temperature and pressure with a reduction in the impurities present in the end product.

More specifically, we have found that the reductive alkylation may be effected using raney nickel as the catalyst at temperatures of the order of 20-30° C. and at pressures from atmospheric up to about 40 psi to produce a product of purity typically greater than 99.5% with a yield of approximately 90%.

The alkyl or substituted alkyl p-aminobenzoates undergoing the reductive alkylation may be produced in situ from a suitable precursor. For example, we have found that alkyl or substituted alkyl p-nitrobenzoates are reduced to the alkyl or substituted alkyl p-aminobenzoate using raney nickel under the same reducing conditions used for the reductive alkylation of the alkyl or substituted alkyl p-aminobenzoate to produce the alkyl or substituted alkyl p-dimethylaminobenzoate. In this way, the process may be carried to completion without isolating the intermediate alkyl or substituted alkyl p-aminobenzoate with considerable benefits for the manufacturer.

The alkyl or substituted alkyl p-dimethylaminobenzoates produced by the process according to the invention have the general formula:

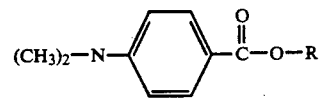

where R is alkyl or substituted alkyl.

Typically R may be any alkyl selected from the group having from 1 to 12 carbon atoms and substituted alkyls may include oxygen and/or nitrogen atoms. Preferably R is ethyl or substituted ethyl, for example butoxyethyl, or amyl (iso or normal).

The invention will now be described in more detail with reference to the following examples of processes according to the invention for the production of ethyl p-dimethylaminobenzoate.

DETAILED DESCRIPTION OF THE EXEMPLARY EMBODIMENTS

EXAMPLE 1

440 gms of benzocaine (ethyl p-aminobenzoate) is stirred in 2 liters of methanol and the mixture purged with nitrogen. 50 gms of raney nickel and 228 gms of 40% formaldehyde are added and the mixture reduced by bubbling in hydrogen at atmospheric pressure or up to 40 psi and cooling to maintain the temperature at 20–30° C. The reaction is monitored by gas or high performance liquid chromatography until complete, adding formaldehyde in further 100 gm portions up to a further 300 gms if required.

At completion, the reaction mixture is warmed to 40–45° C., filtered to remove the raney nickel and the reaction mixture treated with 1 liter of water and 8ml of 0.880 ammonia. The mixture is then cooled to −5° C. slowly and the crystallised ethyl p-dimethylaminobenzoate filtered off, washed with aqueous methanol and dried at 30–40° C. giving a yield of 461 gms (90%) and a purity greater than 99.5% as determined by gas chromatography.

EXAMPLE 2

650 gms of p-nitrobenzoic acid, 1 liter of toluene, 395mls of absolute ethanol and 57 gms of sulphuric acid are stirred and the mixture refluxed for 6-8 hours following which the toluene/water/ethanol ternary azeotrope is removed by distillation over 6-8 hours to drive the esterification reaction to completion. The reaction mixture is then cooled, washed with 1 liter of saturated aqueous sodium bicarbonate solution and the aqueous and organic layers separated. The organic layer is stripped to remove toluene which can be recycled with the residue being ethyl p-nitrobenzoate. Unreacted p-nitrobenzoic acid can be recovered and recycled by acidification of the aqueous layer.

The ethyl p-nitrobenzoate thus obtained is dissolved in 2 liters of methanol and reduced using raney nickel catalyst to ethyl p-dimethylaminobenzoate through the intermediate ethyl p-aminobenzoate using the same reducing conditions described in Example 1. In this way, ethyl p-aminobenzoate is produced in situ as an intermediate reaction product which undergoes the reductive alkylation as described in Example 1 and the process is carried to completion without having to isolate the ethyl p-aminobenzoate. The purity of the ethyl p-dimethylaminobenzoate produced by this route is comparable with that produced starting from benzocaine as described in Example 1.

It will be understood that the invention is not limited to the examples above-described and that other alkyl or substituted alkyl p-dimethylaminobenzoates may be produced by the invented process from the alkyl or substituted alkyl p-aminobenzoate either as starting material or as an intermediate reaction product produced in situ from a suitable precursor as described in the above examples. For example, alkyl or substituted alkyl p-dimethylaminobenzoates where alkyl is selected from the group containing from 1 to 12 carbon atoms, for example amyl (iso or normal) and substituted alkyl having one or more oxygen and/or nitrogen atoms, for example butoxyethyl, may be obtained by the invented process substantially free from impurities.

I claim:

1. A process for the production of alkyl or substituted alkyl p-dimethylaminobenzoates by the reductive alkylation of alkyl or substituted alkyl p-aminobenzoates using formaldehyde in the presence of hydrogen and a catalyst characterised in that the catalyst is raney nickel.

2. A process according to claim 1 wherein the reductive alkylation is effected at a temperature of the order of 20-30° C.

3. A process according to claim 1 wherein the reductive alkylation is effected at pressures from atmospheric up to about 40 psi.

4. A process according to claim 1 wherein the alkyl or substituted alkyl p-aminobenzoate is produced in situ from a precursor.

5. A process according to claim 4 wherein the alkyl or substituted alkyl p-aminobenzoate is produced in situ by reduction of the alkyl or substituted alkyl p-nitrobenzoate.

6. A process according to claim 5 wherein the alkyl or substituted alkyl p-nitrobenzoate is reduced using formaldehyde in the presence of hydrogen and a raney nickel catalyst.

7. A process for the production of alkyl or substituted alkyl p-dimethylaminobenzoates of the general formula:

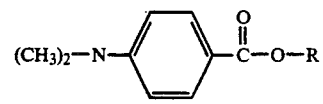

where R is alkyl or substituted alkyl by the reductive alkylation of the alkyl or substituted alkyl p-aminobenzoate using formaldehyde in the presence of hydrogen and raney nickel.

8. A process according to claim 7 wherein R is alkyl having from 1 to 12 carbon atoms.

9. A process according to claim 8 wherein R is selected from the group comprising ethyl, normal amyl and isoamyl.

10. A process according to claim 7 wherein R is substituted alkyl containing at least one member selected from the group consisting of oxygen and nitrogen atoms.

11. A process according to claim 10 wherein R is alkoxy substituted alkyl.

12. A process according to claim 11 wherein R is butoxyethyl ($-CH_2CH_2OCH_2CH_2CH_2CH_3$).

13. A process according to claim 7 wherein the alkyl or substituted alkyl p-dimethylaminobenzoate is obtained with a purity of greater than 99.5%.

* * * * *